United States Patent
Vik et al.

(10) Patent No.: US 11,439,846 B2
(45) Date of Patent: Sep. 13, 2022

(54) VISUALIZATION OF VOLUMETRIC MODULATED ARC THERAPY (VMAT) PLANS

(71) Applicant: KONINKLIJKE PHILIPS N.V., Eindhoven (NL)

(72) Inventors: Torbjoern Vik, Hamburg (DE); Harald Sepp Heese, Hamburg (DE); Christoph Neukirchen, Aachen (DE); Alfonso Agatino Isola, Eindhoven (NL); Rolf Juergen Weese, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 324 days.

(21) Appl. No.: 16/609,910

(22) PCT Filed: May 3, 2018

(86) PCT No.: PCT/EP2018/061442
§ 371 (c)(1),
(2) Date: Oct. 31, 2019

(87) PCT Pub. No.: WO2018/202820
PCT Pub. Date: Nov. 8, 2018

(65) Prior Publication Data
US 2020/0197728 A1     Jun. 25, 2020

Related U.S. Application Data

(60) Provisional application No. 62/500,783, filed on May 3, 2017.

(51) Int. Cl.
*A61N 5/10* (2006.01)

(52) U.S. Cl.
CPC ......... *A61N 5/1047* (2013.01); *A61N 5/1031* (2013.01); *A61N 5/1036* (2013.01); *A61N 5/1081* (2013.01); *A61N 2005/1074* (2013.01)

(58) Field of Classification Search
CPC .......... A61N 5/1031; A61N 2005/1074; A61N 5/103; A61N 5/1081; A61N 5/1036; A61N 5/1047
See application file for complete search history.

(56) References Cited

U.S. PATENT DOCUMENTS

| 7,831,018 | B1 | 11/2010 | Nord |
| 2005/0124861 | A1 | 6/2005 | Breeuwer |

(Continued)

FOREIGN PATENT DOCUMENTS

| WO | 2008130692 A1 | 10/2008 |
| WO | 2009050615 A1 | 4/2009 |

(Continued)

OTHER PUBLICATIONS

International Search Report and Written Opinion of PCT/EP2018/061442, dated Aug. 24, 2018.

*Primary Examiner* — Christine H Matthews
*Assistant Examiner* — Joshua Daryl D Lannu

(57) ABSTRACT

A system includes a computing system with a processor and computer readable storage medium with computer readable and executable instructions, including a radiation plan module, a radiation plan optimization module and a radiation plan visualization module. The processor is configured to execute the instructions, which causes the processor to construct and visually present, via a display monitor, a two-dimensional plot with three-dimensions of data from a radiation plan, and two dimensions along two axes of the plot and a third dimension represented through intensity.

21 Claims, 5 Drawing Sheets

(56) References Cited

U.S. PATENT DOCUMENTS

2013/0077751 A1  3/2013  Gunawardena
2017/0087388 A1  3/2017  Kauppinen

FOREIGN PATENT DOCUMENTS

| WO | 2016008052 A1 | 1/2016 | |
| WO | WO-2016008052 A1 * | 1/2016 | ............. A61B 6/032 |
| WO | 2016046683 A1 | 3/2016 | |

* cited by examiner

VISUALIZATION OF VOLUMETRIC MODULATED ARC THERAPY (VMAT) PLANS

CROSS-REFERENCE TO PRIOR APPLICATIONS

This application is the U.S. National Phase application under 35 U.S.C. § 371 of International Application No. PCT/EP2018/061442, filed on May 3, 2018, which claims the benefit of U.S. Provisional Patent Application No. 62/500,783, filed on May 3, 2017. These applications are hereby incorporated by reference herein.

FIELD OF THE INVENTION

The following generally relates to radiotherapy and more particularly to Volumetric Modulated Arc Therapy (VMAT).

BACKGROUND OF THE INVENTION

Volumetric Modulated Arc Therapy (VMAT) is a delivery type for external beam radiation therapy (EBRT) in which the gantry rotates around a subject and the emitted beam is shaped by moving collimator leaves. A VMAT plan can be described in terms of a set of discrete control points (CP) along an arc, and each CP describing a configuration of the collimator leaf pairs (segment shape), beam intensity (dose rate), and gantry speed. Finding a good and valid VMAT plan is the task of the planner and the optimizer of the treatment planning system (TPS).

Generally, a clinician defines the arc segments to treat (length, position, number of arcs, . . . ), treatment time, number of fractions, and dose objectives measuring dose quality, which machine to use (if the institution has several types of linear accelerators and collimators). A computer-implemented optimization algorithm then proposes a solution taking into account the different constraints, and may have to choose between different equivalent solutions in terms of objective functions (local optimum). The overall process of creating a VMAT plan can therefore be complex, and utilizes many approximations.

To quantify a plan, dose-based metrics like target dose, risk-organ dose, dose homogeneity, etc. have been used. Since dose is only approximated by simulation at the discrete CPs, further metrics on delivery characteristics like delivery time, shape complexity, shape size, shape change, total monitor units (MUs, the total dose emitted from the treatment beam), etc. have been considered. Plan inspection tools include CP spread sheets showing dose rate, gantry angle and maximum leaf speed, graphs of the maximum or average leaf speed, animation of segment shapes, and Digitally Reconstructed Radiographs (DRRs) with superimposed segment shapes.

However, a given plan may not represent a best possible compromise for the constraints. Unfortunately, due to the multi-dimensional nature of the parameters in a plan (e.g., angle and leaf position/movement for each control point, etc.), it may be difficult to understand how a plan is delivered, making it difficult to compare plans and/or understand limiting factors for a given situation. For example, it may be difficult to understand the spatio-temporal succession of segment shapes. Furthermore, the beam intensity may vary temporally, yielding another independent dimension to the data.

SUMMARY OF THE INVENTION

Aspects described herein address the above-referenced problems and/or others.

In one aspect, a system includes a computing system with a processor and computer readable storage medium with computer readable and executable instructions, including a radiation plan module, a radiation plan optimization module and a radiation plan visualization module. The processor is configured to execute the instructions, which causes the processor to construct and visually present, via a display monitor, a two-dimensional plot with three-dimensions of data from a radiation plan, two dimensions along two axes of the plot and a third dimension represented through intensity.

In another aspect, a method includes generating a radiation plan, optimizing the radiation plan, and visualizing the optimized radiation plan by visually displaying a two-dimensional plot with three-dimensions of data from an optimized radiation plan, two dimensions along two axes of the plot and representing a third dimension through intensity.

In another aspect, a computer readable medium is encoded with computer executable instructions which when executed by a processor cause the processor to generate a radiation plan, optimize the radiation plan, and visually summarize the optimized radiation plan by displaying a two-dimensional plot with three-dimensions of data from an optimized radiation plan, two dimensions along two axes of the plot and representing a third dimension through intensity.

These and other aspects will be apparent from and elucidated with reference to an embodiment(s) described herein.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
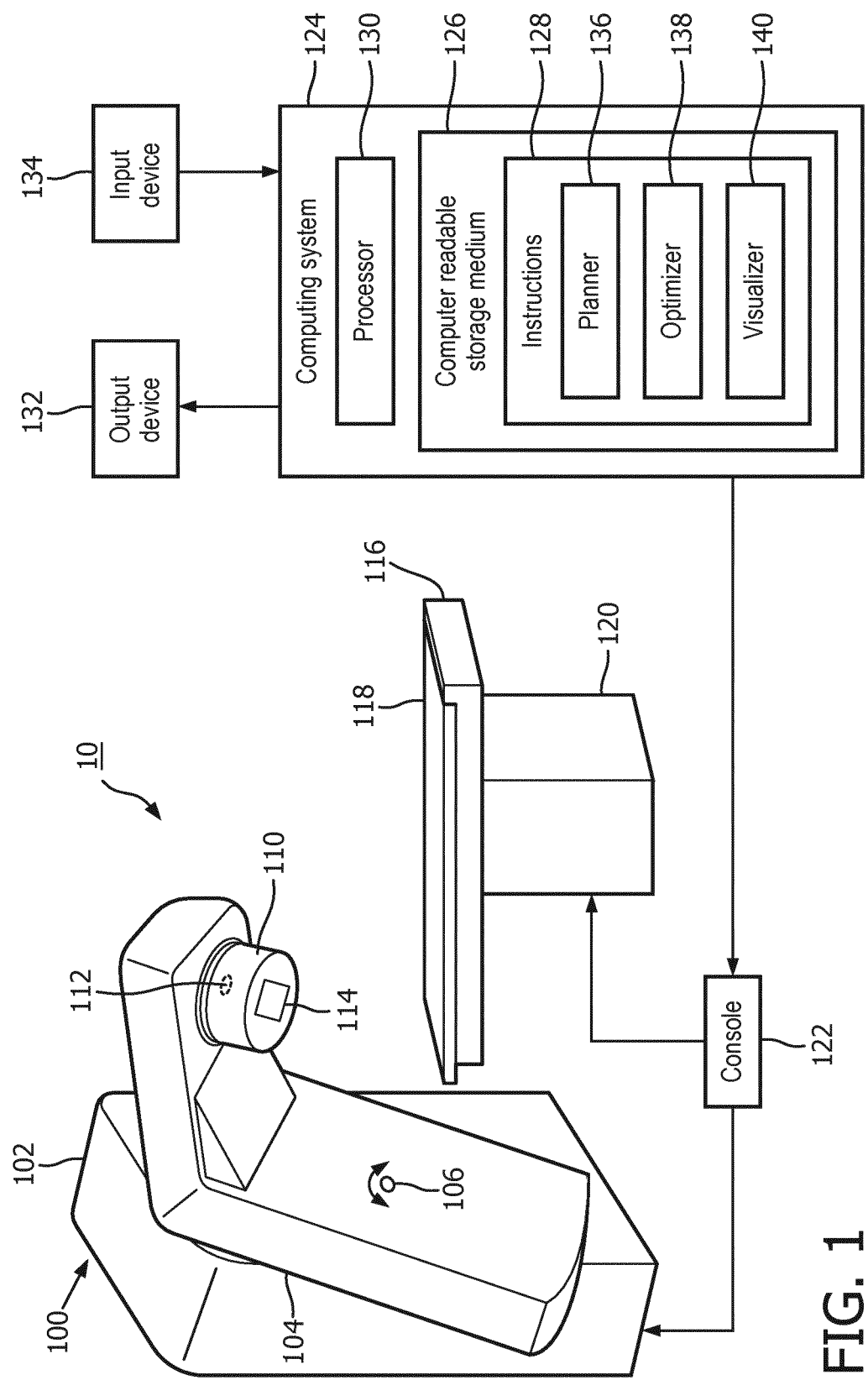
FIG. 1 diagrammatically illustrates an example system which includes a radiotherapy plan visualizer, in accordance with an embodiment(s) described herein.

FIG. 1 schematically illustrates a system 10 with a radiation therapy system 100 such as a linear accelerator (LINAC) and a treatment planning system (TPS), which is shown in this example as a computing system 124. The radiation therapy system 100 includes a stationary gantry 102 and a rotating gantry 104, which is rotatably attached to the stationary gantry 102. The rotating gantry 104 is configured to rotate (e.g., 360°, or more or less) with respect to a rotation axis 106 about a treatment region 108.

The rotating gantry 104 includes a treatment head 110 with a therapy (e.g., a megavolt (MV)) radiation source 112 that delivers treatment radiation and a collimator 114 (e.g., a multi-leaf collimator) that can shape the radiation fields that exit the treatment head 110 into predetermined shapes. The radiation source 112 rotates in coordination with the rotating gantry 104 about the treatment region 108. The collimator 114 includes a set of jaws and multiple leaves that can both move independently to shape a field.

A subject support 116, such as a couch, supports a portion of a subject in the treatment region 108. The illustrated patient support 116 includes a tabletop 118 and a base 120. The tabletop 118 is configured to translate in and out of the treatment region 108.

An operator console 122 (e.g., a computer) includes human readable output devices such as a display and input devices such as a keyboard and/or mouse. Software accessible on the console 122 allows the operator to control an operation of the radiation therapy system 100. For example, the console 122 can be used to load a VMAT, IMRT, etc. treatment plan. The console 122 controls, based on the plan, gantry rotation, collimation, and treatment delivery, etc. at control points along an arc(s).

The computing system 124 includes a computer readable storage medium 126 (which excludes transitory medium), such as physical memory and/or other non-transitory memory. The computer readable storage medium 126 stores computer executable instructions ("instructions") 128. The computing system 124 further includes a processor 130 (e.g., a central processing unit or CPU, a microprocessor, a controller, or the like), which is configured to execute the instructions 128. The computing system 124 further includes an output device 132 (e.g., a display monitor) and an input device 134 (e.g., a mouse, keyboard, etc.).

The instructions 128 include a radiation treatment plan module ("planner") 136, a radiation treatment plan optimizer module ("optimizer") 138, and a radiation treatment visualization module ("visualizer") 140. The planner 136 creates a radiation treatment plan(s) based on user input such as an arc segment(s), a control point(s) along each arc segment, a treatment time, a number of fractions, a dose objective measuring dose quality, a treatment delivery machine characteristic, etc. The optimizer 138 processes the radiation treatment plan(s) and proposes a solution(s) taking into account the different constraints.

The visualizer 140 constructs and visually presents a summary of delivery characteristics of the optimized radiation treatment plan(s). This includes creating different types of two-dimensional (2-D) plots from three or more different dimensions of data from the radiation treatment plan(s). As described in greater detail, in one instance, a plot(s) show characteristics such as leaf opening characteristics (e.g. statistics) of a complete VMAT arc, e.g., by explicitly visualizing both control point-index/gantry angle (time axis) and one of the spatial axes of the multi-leaf collimator (leaf pair index, or position on leaf travel axis), while another spatial dimension is collapsed into a single numeric value, which defines an intensity (e.g. gray or color scale) at a parameter combination.

In one instance, such plots are informative, providing a comprehensive visual summary of radiation treatment plan delivery characteristics. The comprehensive visual summary may improve the understanding of how a radiation treatment plan(s) is delivered and/or facilitate comparing radiation treatment plans, e.g., for different trials, arcs, settings, etc. A trial, generally, is an alternative plan where the machine, arc definition, collimator angle, delivery time and/or any other setting might be different. For each of these settings, the optimizer finds an optimal solution, but it does not optimize over these settings (i.e. it finds the best possible setting, at the choice of the planner). The visualization may take into account more information than techniques involving control point spread sheets, plots of maximum or average leaf travel, segment shape animations, etc. As such, in one instance, the approach described herein may facilitate the process of radiotherapy planning and/or accepting a radiation treatment plan(s), and/or simplifying quality assurance (QA) before delivery.

Although FIG. 1 shows the console 122 and the computer system 124 as separate components of the system 10, in a variation, the console 122 and the computing system 124 are part of a same computing system (e.g., the console 122 or the computing system 122). In another variation, the computing system 124 and/or the radiation therapy system 100 may be separate and distinct from the system 10. Furthermore, the computing system 124 may be located near (in the same room, a neighboring room, etc.) or remote (e.g., in a more distant room, in a different facility, etc.) from the console 122.

FIGS. 2, 3, 4 and 5 illustrate non-limiting examples of summaries constructed and visually presented with the visualizer 140. For explanatory purposes and sake of brevity, the illustrated summaries summarize a radiation treatment plan (s) with two planning target volumes (PTVs) and a single arc with multiple control points.

Figure 2:
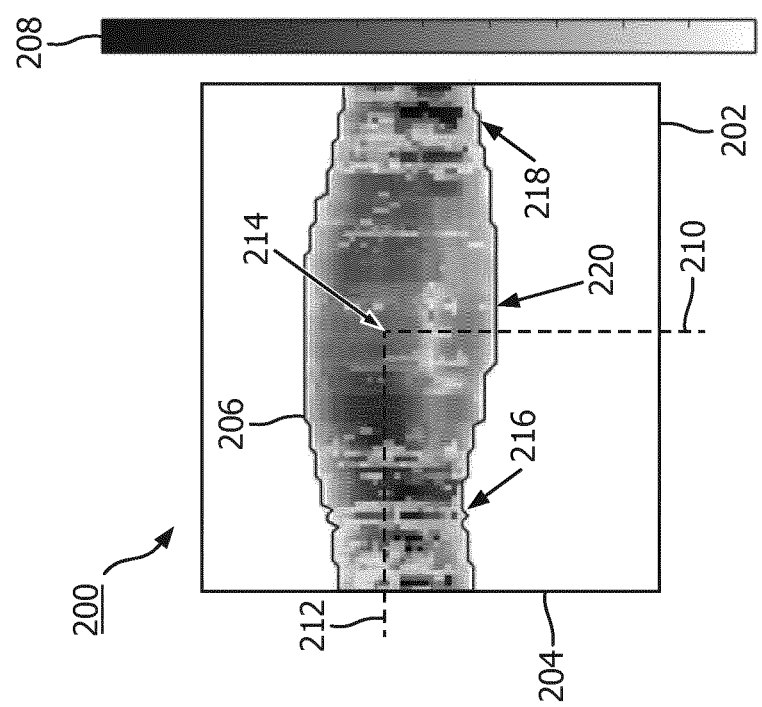
FIG. 2 depicts a plot constructed and presented by the plan visualizer collapsing three-dimensional plan data into a two-dimensional plot with intensity representing a third dimension, in accordance with an embodiment(s) described herein.

For FIG. 2, the visualizer 140 constructs and presents a plot 200 of leaf pair opening size as a function of control points and collimator rows.

A first (or x—) axis 202 represents control points. A second (or y—) axis 204 represents collimator rows/leaf pairs. An envelope 206 represents positions of top and bottom jaws of the collimator. Leaf pair opening size is represented in the plot 200 through intensity using a gray scale, where white indicates a shortest opening size (or fully closed), black indicates a largest opening size (or fully open), and gray levels there between indicate an increasing opening from lighter shades of gray to darker shades of gray (or a decreasing opening from darker shades of gray to lighter shades of gray).

A legend 208 indicates the visualized levels of gray, which may be the entire range from white to black, or a sub-range from white or a first gray level to black or a second darker gray level. Values outside the envelope 206 are white size since these regions are outside of the envelope 206 jaws. For a particular control point 210 and a particular collimator row leaf pair 212, a relative opening size of the leaf pair is indicated by a gray scale value at 214. In this particular example, the plot 200 indicates larger leaf pair openings in first and second regions 216 and 218, relative to a region 220, since the regions 216 and 218 include the darker intensities.

In one instance, a degree of variation in opening size at neighboring control points may indicate further optimization should be considered, e.g., since large leaf movement has been associated with less accurate dose simulation. In general, the plot 200 collapses three-dimensions of data into a 2-D plot, where a third dimension is represented through intensity. In a variation, a color scale is used to represent intensity. Two or more such plots can be concurrently displayed for comparative purposes. For example, plots for different arcs (where there are multiple arcs) can be simultaneously displayed side-by-side. In another example, plots for different trials with different delivery times can be displayed side-by-side and the choices made by the optimizer can be compared visually.

In one instance, a range of one or both of the axes 202 and 204 can be configurable. As such, one or both of the axes 202 and 204 can represent the entire range of leaf pair and control points. In another instance, at least one of the axes 202 and 204 can represent a patch or sub-set of (less than) the entire range. In yet another instance, at least one of the axes 202 and 204 can represent multiple sub-sets of the entire range, and not the entire range. Instead of or in addition to control point index, gantry angle can be used as first—(or x—) axis. Other information, such as a plot of the monitoring units (MUs), an average and/or maximum value of an opening size, a total MU value, etc. can be displayed superimposed a region of a plot.

Figure 3:
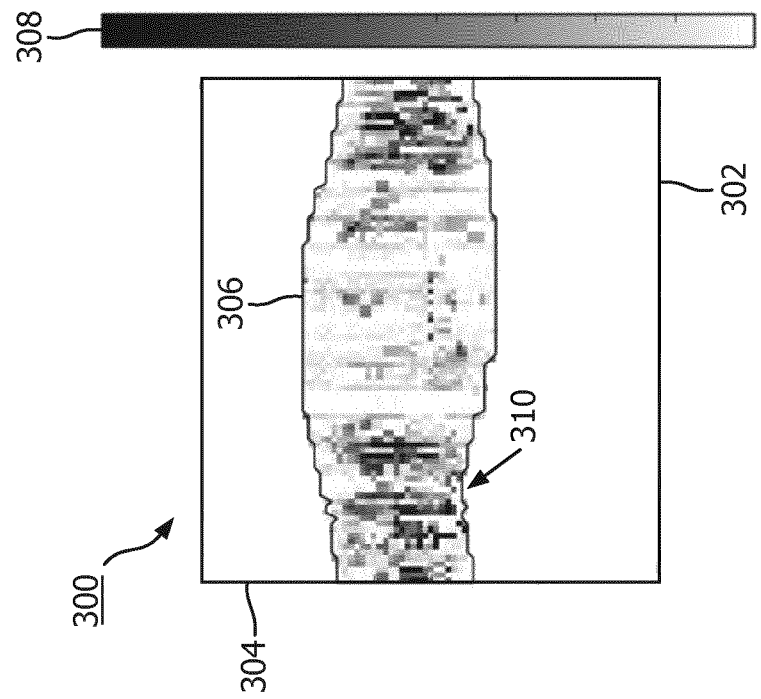
FIG. 3 depicts another plot constructed and presented by the plan visualizer collapsing three-dimensional plan data into a two-dimensional plot with intensity representing a third dimension, in accordance with an embodiment(s) described herein.

FIG. 3 shows a plot 300, which is substantially similar to the plot 200, except the collapsed third dimension represents a displacement or change in leaf pair opening between control points, and the gray scale is reversed.

A first axis 302 represents control points, a second axis 304 represents a collimator rows/leaf pairs, and an envelope 306 represents positions of top and bottom jaws of the collimator. Change in leaf pair opening size is represented in the plot 300 through intensity using a gray scale, where white indicates a smallest change, black indicates a largest change, and gray levels there between indicate an increasing change from lighter shades of gray to darker shades of gray. A legend 308 indicates the visualized levels of gray. In one instance, the intensity is calculated as a sum of left and right displacements.

This particular example shows segment weights seem to oscillate between a region 310 of control points where there is large leaf movement. This could be an indication to increase the value of the temporal smoothing parameter before optimization. By taking a derivative(s) over two or more (user selected and/or default) control points; the intensity in the plot 300 (or a new plot(s)) shows velocity (derivative of displacement) and/or acceleration (derivative of velocity) instead of leaf pair displacement between control points.

Figure 4:
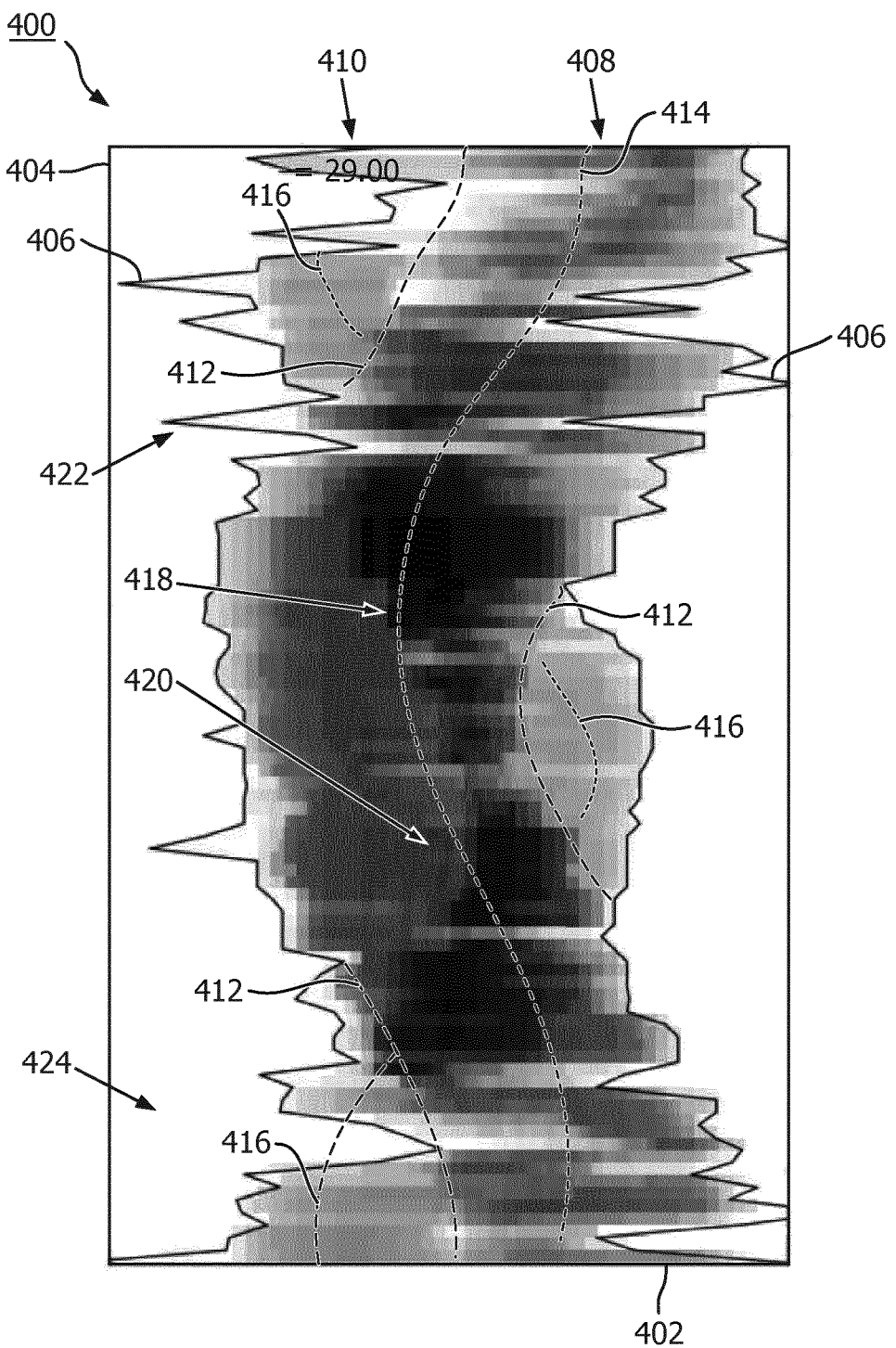
FIG. 4 depicts yet another plot constructed and presented by the plan visualizer collapsing three-dimensional plan data into a two-dimensional plot with intensity representing a third dimension, in accordance with an embodiment(s) described herein.

For FIG. 4, the visualizer 140 constructs and presents a plot 400 of number of open leaf pairs as a function of leaf travel position and gantry angle for the two planning target volumes (PTVs).

A first axis 402 represents a discretized leaf travel positions. A second axis 404 represents control point gantry angle. The visualizer 140 discretizes leaf-travel direction and counts a number of open rows at each position for each control point gantry angle. The (gray scale) intensity of the plot 400 corresponds to this count. Left and right carriage movement are indicated by outline 406.

The plot 400 shows a larger PTV with a trajectory 408 from right-left-right going from top to bottom, and a smaller PTV with a trajectory 410 from left-right-left going from top to bottom. In plot 400, "dashed lines" 412 and the "dotted lines" 414 and 416 are provided solely as a visually aid in this explanation to help distinguish the trajectories 408 and 410. The lines 412 help distinguish between the two PTVs, and the lines 414 and 416 help visualize the trajectory paths. These lines may or may not be part of the plot 400.

This particular example shows the largest openings of the two PTVs are at (darker) regions 418 and 420 where the two trajectories 408 and 410 cross. This particular example also shows the optimizer 138 has difficulties finding a smooth solution between the PTV's in regions 422 and 424. By taking a difference between control points, the plot 400 (or a new plot) shows changes from open to close and/or close to open. In a variation, the plot 400 can show a trajectory for only a single PTV or trajectories for more than two PTVs.

Figure 5:
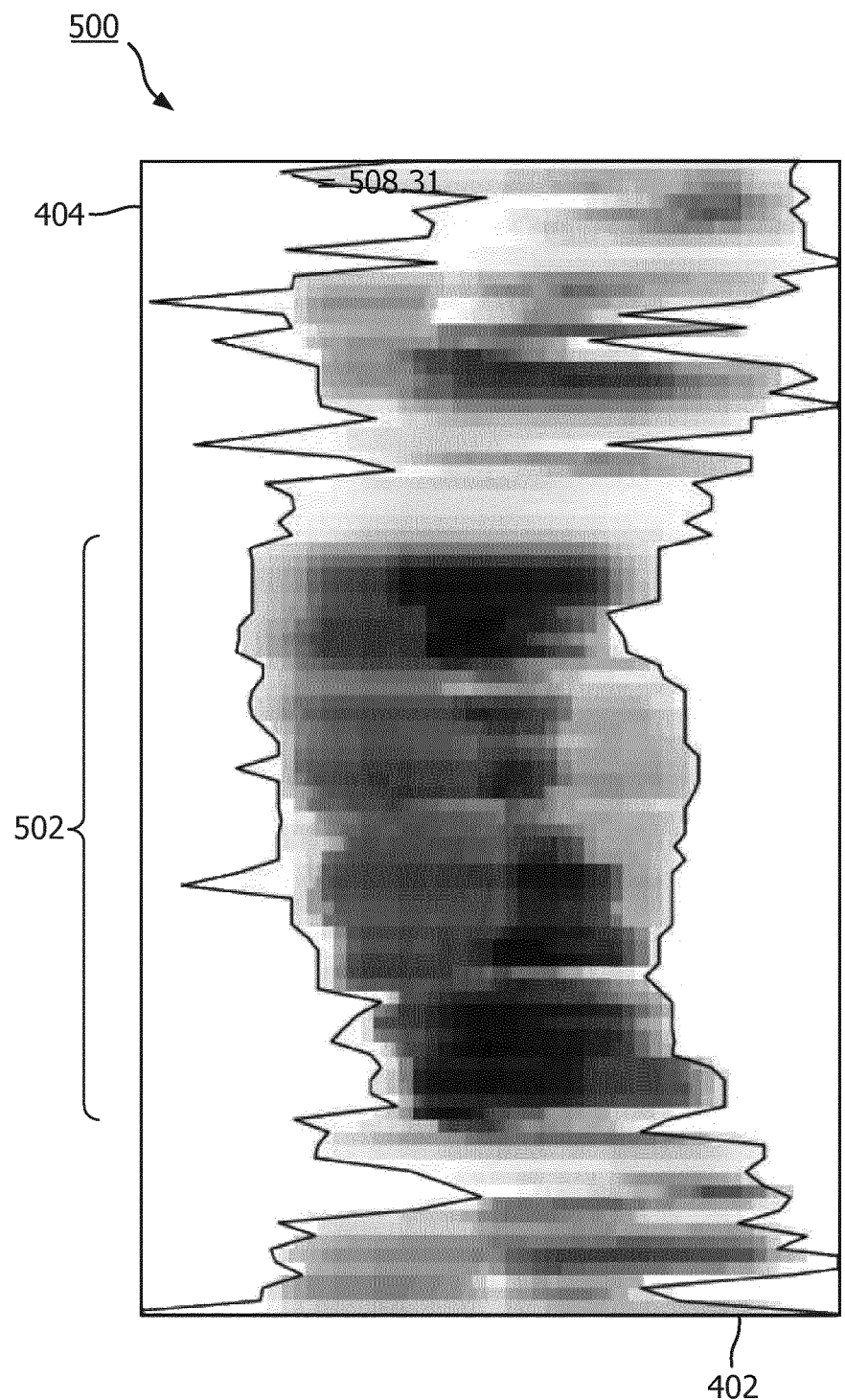
FIG. 5 depicts still another plot constructed and presented by the plan visualizer collapsing three-dimensional plan data into a two-dimensional plot with intensity representing a third dimension, in accordance with an embodiment(s) described herein.

For FIG. 5, the visualizer 140 constructs and presents a plot 500 computed by weighting the intensities at each control point in the plot 400 by the control point monitor units.

In one instance, this gives additional information on arc segments that the optimizer prefers for treatment. This particular example shows main arc segments for treatment are in a region 502. Where the axis 402 is for 360 degrees, these segments indicate the optimizer 138 determined most of the treatment (dose) is to be provided in approximately 180 degrees of a middle section of the 360 arc. Such information may be difficult to read without collapsing into the 2-D plot 500. This may lead to adding another arc to the plan for the region 502.

Figure 6:
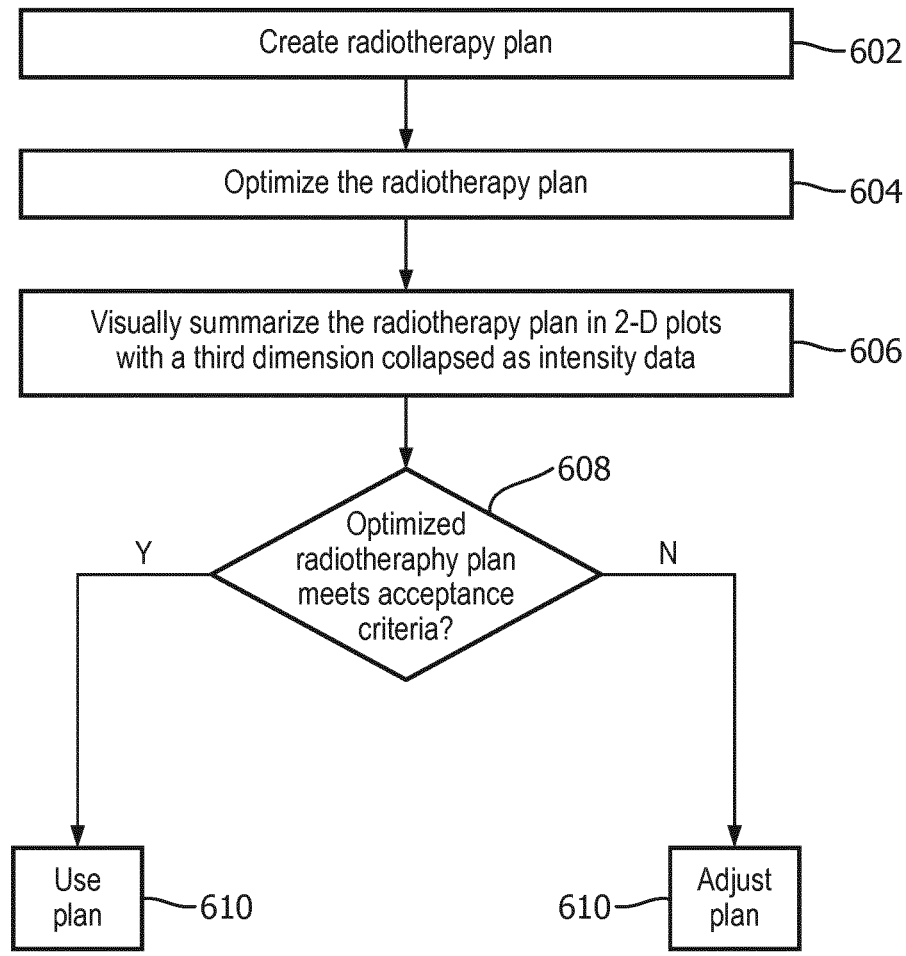
FIG. 6 illustrates a method in accordance with an embodiment(s) described herein.

FIG. 6 illustrates an example method in accordance with an embodiment herein.

At 602, a radiotherapy plan is created with the planner 136.

At 604, the radiotherapy plan is optimized with the optimizer 138.

At 606, the optimized radiotherapy plan is visually summarized with the visualizer 140, as described herein and/or otherwise.

At 608, it is determined if the plan meets acceptance criteria.

At 610, the radiotherapy plan is utilized if the plan meets the acceptance criteria. It is to be appreciated that the plan can be adjusted, deleted and/or not used even if the acceptance criteria is met.

At 612, the radiotherapy plan is adjusted if the plan did not meet the acceptance criteria. It is to be appreciated that the plan can be used even if the acceptance criteria is not met. Some of the above may be implemented by way of computer readable instructions, encoded or embedded on computer readable storage medium (which excludes transitory medium), which, when executed by a computer processor(s), cause the processor(s) to carry out the described acts. Additionally or alternatively, at least one of the computer readable instructions is carried by a signal, carrier wave or other transitory medium.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A planning system for planning external beam radiation therapy by a radiation therapy system, the planning system comprising:
    a processor in communication with a display monitor; and
    a non-transitory computer readable storage medium storing computer readable and executable instructions that, when executed by the processor, cause the processor to:
    receive a proposed optimized radiation treatment plan for use in external beam radiation therapy, taking into account constraints; and
    construct and visually present, via the display monitor, a two-dimensional plot with three-dimensions of data based at least in part on control parameters of a collimator of the radiation therapy system from the optimized radiation treatment plan,
    wherein first and second dimensions are plotted along first and second axes of the plot and a third dimension is indicated through intensity of gray scale or color scale of the plot on the display monitor to provide a comprehensive visual summary of delivery characteristics of the optimized radiation treatment plan to a user for identifying a desirable radiation treatment plan.

2. The planning system of claim 1, wherein the control parameters are for a volumetric modulated arc therapy beam.

3. The planning system of claim 1, wherein the collimator comprises a multi-leaf collimator.

4. The planning system of claim 3, wherein the three-dimensions of data include leaf pair opening size, control points, and collimator rows of the multi-leaf collimator.

5. The planning system of claim 4, wherein the first axis of the plot indicates the control points, the second axis of the plot indicates the collimator rows, and the intensity indicates the leaf pair opening size.

6. The planning system of claim 4, wherein the plot further includes an envelope which showing top and bottom positions of jaws of the multi-leaf collimator.

7. The planning system of claim 6, wherein the optimized radiation treatment plan includes a plurality of alternative treatment plans, and
    wherein the instructions further cause the processor to construct and visually present, via the display monitor, additional two-dimensional plots with three-dimensions of data for each alternative treatment plan of the plurality of alternative treatment plans, and the additional plots are concurrently visually presented.

8. The planning system of claim 3, wherein the three-dimensions of data include control points, change in leaf pair opening between the control points, and collimator rows of the multi-leaf collimator.

9. The planning system of claim 8, wherein the first axis of the plot indicates the control points, the second axis of the plot indicates the collimator rows, and the intensity indicates the change in leaf pair opening between the control points, and wherein the instructions cause the processor to further determine velocity based on the change in leaf pair opening between control points.

10. The planning system of claim 8, wherein the first axis of the plot indicates the control points, the second axis of the plot indicates the collimator rows, and the intensity indicates an acceleration of leaf pairs of the of the multi-leaf collimator, and wherein the instructions cause the processor to further determine velocity based on the change in the leaf pair opening between the control points.

11. The planning system of claim 8, wherein the intensity is weighted at each control point by control point monitor units.

12. The planning system of claim 1, wherein the optimized radiation treatment plan includes a plurality of arcs, and
    wherein the instructions further cause the processor to construct and visually present, via the display monitor, additional two-dimensional plots with three-dimensions of data for each arc of the plurality of arcs, and the additional plots are concurrently visually presented.

13. The planning system of claim 1, wherein the three-dimensions of data include discretized leaf travel positions of a collimator, control point gantry angles at control points along an arc, and a number of open leaf pairs of the collimator, and wherein the first axis of the plot indicates the discretized leaf travel positions, the second axis of the plot indicates the control point gantry angles, and the intensity indicates a number of open leaf pairs.

14. A method for planning external beam radiation therapy by a radiation therapy system, the method comprising:
    receiving a proposed optimized radiation treatment plan for use in external beam radiation therapy; and
    visualizing the optimized radiation treatment plan by visually displaying on a display monitor a two-dimensional plot with three-dimensions of data based at least in part on control parameters of a collimator of the radiation therapy system from the optimized radiation treatment plan,
    wherein first and second dimensions are plotted along first and second axes of the plot and a third dimension is indicated by intensity of gray scale or color scale of the plot on the display monitor to provide a comprehensive visual summary of delivery characteristics of the optimized radiation treatment plan to a user for identifying a desirable radiation treatment plan.

15. The method of claim 14, wherein the first axis of the plot indicates control points, the second axis of the plot indicates collimator rows of the collimator, and the intensity indicates leaf pair opening size of the collimator.

16. The method of claim 14, wherein the first axis of the plot indicates control points, the second axis of the plot indicates collimator rows of the collimator, and the intensity indicates change in leaf pair opening between the control points.

17. The method of claim 14, wherein the first axis of the plot indicates discretized leaf travel positions of the collimator, the second axis of the plot indicates control point gantry angles of control points, and the intensity indicates a number of open leaf pairs of the collimator.

18. A non-transitory computer readable medium storing computer executable instructions, for planning external beam radiation therapy by a radiation therapy system, which when executed by a processor cause the processor to:
    receive a proposed optimized radiation treatment plan for use in external beam radiation therapy; and
    visually summarize the optimized radiation treatment plan on a display monitor by displaying a two-dimensional plot with three-dimensions of data based at least in part on control parameters of a collimator of the radiation therapy system from the optimized radiation treatment plan,
    wherein first and second dimensions are plotted along first and second axes of the plot and a third dimension is indicated by intensity of gray scale or color scale of the plot on the display monitor to provide a comprehensive visual summary of delivery characteristics of the optimized radiation treatment plan to a user for identifying a desirable radiation treatment plan.

19. The computer readable medium of claim 18, wherein the first axis of the plot indicates control points, the second axis of the plot indicates collimator rows of the collimator, and the intensity indicates leaf pair opening size of the collimator.

20. The computer readable medium of claim 18, wherein the first axis of the plot indicates control points, the second axis of the plot indicates collimator rows of the collimator, and the intensity indicates change in leaf pair opening between the control points.

21. The computer readable medium of claim 18, wherein the first axis of the plot indicates discretized leaf travel positions of the collimator, the second axis of the plot indicates control point gantry angles, and the intensity indicates a number of open leaf pairs of the collimator.

* * * * *